(12) United States Patent
Schoenmeyer et al.

(10) Patent No.: US 9,740,912 B2
(45) Date of Patent: Aug. 22, 2017

(54) EVALUATION OF CO-REGISTERED IMAGES OF DIFFERENTLY STAINED TISSUE SLICES

(75) Inventors: Ralf Schoenmeyer, Garching (DE); Gerd Binnig, Kottgeisering (DE); Guenter Schmidt, Munich (DE); Maria Athelogou, Munich (DE); Peter Ellenberg, Munich (DE)

(73) Assignee: Definiens AG, Munich (DE)

( * ) Notice: Subject to any disclaimer, the term of this patent is extended or adjusted under 35 U.S.C. 154(b) by 1442 days.

(21) Appl. No.: 13/330,900

(22) Filed: Dec. 20, 2011

(65) Prior Publication Data

US 2013/0156279 A1 Jun. 20, 2013

(51) Int. Cl.
| | |
|---|---|
| G06K 9/00 | (2006.01) |
| G06K 9/34 | (2006.01) |
| G06T 17/00 | (2006.01) |
| G09G 5/00 | (2006.01) |
| G06T 7/33 | (2017.01) |

(52) U.S. Cl.
CPC ............. *G06K 9/0014* (2013.01); *G06T 7/33* (2017.01); *G06T 2207/10056* (2013.01); *G06T 2207/30024* (2013.01)

(58) Field of Classification Search
CPC .................... G06T 7/0028; G06T 2207/30024
See application file for complete search history.

(56) References Cited

U.S. PATENT DOCUMENTS

| | | | | |
|---|---|---|---|---|
| 6,243,095 B1* | 6/2001 | Shile et al. | ................... | 715/854 |
| 7,249,317 B1* | 7/2007 | Nakagawa et al. | ........... | 715/209 |
| 2005/0270639 A1 | 12/2005 | Miki | ............................. | 359/381 |
| 2005/0271356 A1* | 12/2005 | Koresawa et al. | ............... | 386/46 |
| 2007/0297672 A1 | 12/2007 | Eschbach et al. | ............ | 382/173 |
| 2008/0032328 A1 | 2/2008 | Cline et al. | ................... | 435/40.5 |
| 2009/0245610 A1* | 10/2009 | Can et al. | ...................... | 382/133 |

(Continued)

FOREIGN PATENT DOCUMENTS

EP 2333717 11/2009

OTHER PUBLICATIONS

Steve Eddins, "Steve on Image Processing: Gray scale pixel values in labeled regions," Aug. 21, 2007 Mathworks Blog, downloaded on Jul. 22, 2013 from http://blogs.mathworks.com/steve/2007/08/21/gray-scale-pixel-values-in-labeled-regions/ XP002704903 (4 pages).

(Continued)

*Primary Examiner* — Tapas Mazumder
(74) *Attorney, Agent, or Firm* — Imperium Patent Works; Darien K. Wallace

(57) ABSTRACT

A method for co-registering images of tissue slices stained with different biomarkers displays a first digital image of a first tissue slice on a graphical user interface such that an area of the first image is enclosed by a frame. Then a portion of a second image of a second tissue slice is displayed such that the area of the first image enclosed by the frame is co-registered with the displayed portion of the second image. The displayed portion of the second image has the shape of the frame. The tissue slices are both z slices of a tissue sample taken at corresponding positions in the x and y dimensions. The displayed portion of the second image is shifted in the x and y dimensions to coincide with the area of the first image that is enclosed by the frame as the user shifts the first image under the frame.

17 Claims, 10 Drawing Sheets

(56) References Cited

U.S. PATENT DOCUMENTS

2009/0316962 A1* 12/2009 Sun et al. .................. 382/118
2010/0215227 A1    8/2010 Grunkin et al. ............ 382/128
2011/0128299 A1*  6/2011 Wakita et al. .............. 345/629
2012/0179665 A1*  7/2012 Baarman et al. ............ 707/709

OTHER PUBLICATIONS

Wikipedia: Immunohistochemistry, Dec. 4, 2011 downloaded on Jul. 22, 2013 from http://en.wikipedia.org/w/index.php?title=Immunohistochemistry?oldid=463985146 XP002704902 (6 pages).

Extended European Search Report (EESR) dated Aug. 26, 2014 from EPO in related foreign application EP12197658.3 (9 pages).

Johnson et al., "Development of Feature Analysis on Consecutive Tissue Sections (FACTS)," Flagship Biosciences LLC, 2010, downloaded from http://www.flagshipbio.com/wp-content/uploads/2009/12/DP2010-Poster-1_Development-and-Validation-of-FACTS.pdf on Dec. 16, 2011 (1 page).

Arganda-Carreras et al, "Automatic registration of serial mammary gland sections," Proceedings of the 26$^{th}$ Annual Int'l Conf. of the IEEE EMBS, San Francisco Sep. 1-5, 2004, vol. 3, pp. 1691-1694 XP010775280 (4 pages).

Yuan Zhen-ming et al., "Multi-sensor image registration using multi-resolution shape analysis," Journal of Zhejiang University Science A, vol. 7, No. 4 Mar. 14, 2006 pp. 549-555 XP036040674 (7 pages).

Partial European Search Report dated Jun. 22, 2017 from EPO in related foreign application EP17161436.5 (15 pages).

* cited by examiner

EVALUATION OF CO-REGISTERED IMAGES OF DIFFERENTLY STAINED TISSUE SLICES

TECHNICAL FIELD

The present invention relates to displaying digital images of co-registered slides of stained tissue so as to enable the simultaneous inspection of how multiple biomarkers stain the same tissue location.

BACKGROUND

It is becoming increasingly important in pharmacology, anatomical pathology and biopharmaceutical research to analyze human tissue samples that are stained with multiple biomarkers. How the same tissue sample reacts to staining by different biomarkers can be determined by slicing the tissue into multiple very thin slices in the z dimension and then separately staining the slices. The correlated analysis of different biomarker staining provides a higher quality medical evaluation than separately analyzing how the same tissue reacts to different biomarkers.

In order to determine how different biomarkers stain the same tissue structures, however, digital images of the slices must be co-registered to indicate which tissue structures in one slice correspond to the tissue structures in the other slices. Co-registration of the digital images is possible only if the thickness of the slices is very thin such that cross sections of the same structures will appear in the digital images of multiple slices. For example, multiple slices may pass through the membrane of a single cell, and it may be possible to determine that the various membrane outlines correspond to the same cell even though the membrane outlines are not identical. Co-registration of the digital images involves mapping of pixels from the digital image of one slice to the related pixels of the digital image of the adjacent slice. Spatial translation and rotation transforms are defined that maximize cross-correlation between corresponding structures in the two images by mapping the pixels from one image to the corresponding pixels of the other image.

Determining corresponding tissue structures to use for co-registration, however, is computationally intensive because digital images of tissue slices typically have a very high spectral resolution, which can be on the order of several Giga-pixels. Performing segmentation on all of the structures in images of adjacent slices and then comparing each structure in one image to all of the structures in the other image to find corresponding structures would not be computationally feasible. Thus, segmentation is typically performed on low-resolution superimages of the tissue slices in order to find structures to use for co-registration. But co-registration performed using low-resolution structures is consequently imprecise. A precise method of co-registration is sought that does not require the segmentation of entire high-resolution images of adjacent tissue slices.

An object-based analysis of the stained structures in each image is performed that allows the results of the different staining to be visually enhanced for better correlation. Once the images of differently stained tissue slices are segmented, enhanced and co-registered, the physician or researcher views the different results on the same structures to make a medical evaluation. A method is sought for displaying the various different staining results to the physician or researcher that simultaneously depicts corresponding structures in the various digital images of differently stained tissue.

SUMMARY

A system for co-registering and displaying digital images of tissue slices stained with different biomarkers permits the user simultaneously to view portions of the co-registered images. In one embodiment, a first digital image of a first tissue slice is displayed on a graphical user interface such that an area of the first digital image is enclosed by a frame. Then a portion of a second digital image of a second tissue slice is displayed on the graphical user interface such that the area of the first digital image that is enclosed by the frame is co-registered with the displayed portion of the second digital image. Consequently, the area of the first digital image that is enclosed by the frame corresponds to the displayed portion of the second digital image. The displayed portion of the second digital image has the shape of the frame. The first tissue slice and the second tissue slice are both z slices taken from a tissue sample at corresponding positions in the x and y dimensions. The displayed portion of the second digital image is shifted in the x and y dimensions to coincide with the area of the first digital image that is enclosed by the frame as the user of the system shifts the frame in the x and y dimensions over the first digital image.

In another embodiment, the user of the system shifts the first digital image under a stationary frame on the graphical user interface. The first digital image of the first tissue portion is displayed on the graphical user interface such that an area of the first digital image is enclosed by the frame. A second digital image of a second tissue portion is also displayed on the graphical user interface. A third digital image of a third tissue portion is displayed on the graphical user interface adjacent to the second digital image in a row above the first digital image. The first, second and third tissue portions are all z slices taken from a tissue sample at corresponding positions in the x and y dimensions. Each of the second and third digital images has the shape of the frame that is positioned towards the middle of the graphical user interface. The area of the first digital image that is enclosed by the frame is co-registered with both the second digital image and the third digital image. The system shifts both the second and third images such that the visible portions of the second and third images in the row above the first image coincide with the area of the first image that is enclosed by the frame as the user shifts the first digital image in the x and y dimensions under the frame.

In yet another embodiment, the system navigates to a tile region in a digital image that corresponds to a selected tile of a tiled representation of the digital image that the user has selected. A portion of a digital image of a stained tissue slice is displayed on a graphical user interface. The digital image is divided into tile regions. The system generates a statistical value for each of the tile regions of the digital image. For example, the statistical value represents the manner in which the particular tile region has been stained by a biomarker. A tiled representation of the digital image is also displayed on the graphical user interface. Each tile of the tiled representation corresponds to a tile region of the digital image and has an appearance indicative of the statistical value associated with the corresponding tile region. For example, the color of a tile indicates the range in which the statistical value associated with the corresponding tile region falls. A selected tile on the tiled representation corresponds to a first tile region of the digital image that is outside the field of view of the graphical user interface. In response to the user selecting the selected tile, the system shifts the digital image such that the first tile region moves into the field of view of the graphical user interface.

In yet another embodiment, the system navigates to a region in a higher resolution image that corresponds to a location on a corresponding lower resolution image that the user has selected. The system displays on a graphical user interface a portion of a higher resolution image of a tissue slice that has been stained with a biomarker. The higher resolution image is divided into regions. The system then generates a statistical value associated with each of the regions. For example, the statistical value is a staining score. The system generates a lower resolution image from the higher resolution image such that each location on the lower resolution image corresponds to a region of the higher resolution image. Each location on the lower resolution image has an appearance indicative of the statistical value associated with the corresponding region on the higher resolution image. In one situation, a selected location on the lower resolution image corresponds to a first region on the higher resolution image that is not visible because the first region is outside the field of view of the graphical user interface. In response to a user selecting the selected location on the lower resolution image, the system shifts the higher resolution image on the graphical user interface such that the first region moves into the field of view and becomes visible on the graphical user interface.

In yet another embodiment, the system performs co-registration on two higher resolution images of differently stained tissue slices. The image analysis program of the system generates first and second lower resolution images from first and second higher resolution images of first and second tissue slices, respectively. Using digital image analysis, the system defines a first shape within the first lower resolution image and a second shape within the second lower resolution image. The image analysis program determines that the first shape corresponds to the second shape. A first region in the first higher resolution image is defined using the first shape within the first lower resolution image, and a second region in the second higher resolution image is defined using the second shape within the second lower resolution image.

The image analysis program then determines co-registration parameters for co-registering the second high resolution digital image with the first high resolution digital image using the first and second regions. Corresponding tissue structures are identified in the first and second regions. By mapping the tissue structures in the second region to the corresponding tissue structures in the first region, all of the positions in the second higher resolution image are interpolated linearly. The co-registration of the second higher resolution image is performed by translating, rotating and scaling the second higher resolution image into a common coordinate system with the first higher resolution image. The display module of the system then uses the co-registration parameters to display a portion of the first high resolution digital image and a portion of the second high resolution digital image in a co-registered orientation on a graphical user interface.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
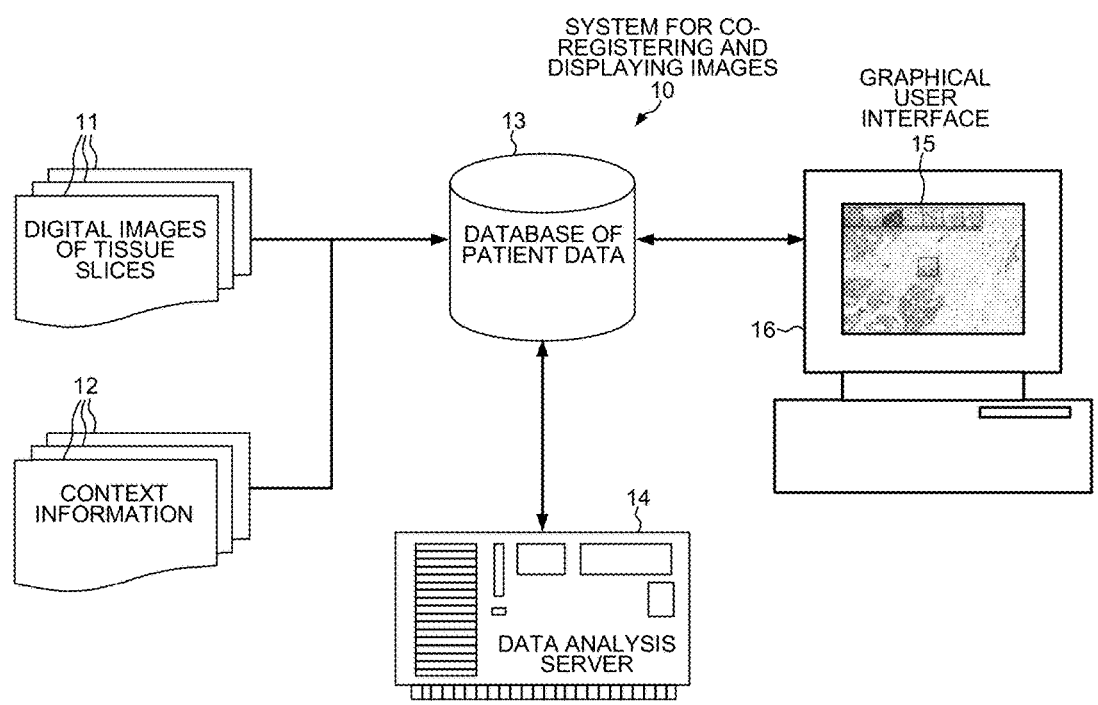
FIG. 1 is a diagram of a novel system for co-registering and displaying digital images of tissue slices stained with different biomarkers.

FIG. 1 shows a system 10 for co-registering and displaying digital images of tissue slices stained with different biomarkers. The images 11 can be acquired using various imaging devices, such as a regular light microscope, a computed tomography (CT) device, a magnetic resonance imaging (MRI) device, or a positron emission tomography (PET) device. For example, the images are obtained from tissue slices used in pathology or from CT scans used in radiology. Input data for the image analysis can also include patient medical history and demographic data that is used as context information 12 for calculating parameters used in the image analysis. For example, identifying cancer cells in a sample of breast tissue can be assisting by knowing whether the patient smokes or breast fed her children.

The acquired digital images 11 as well as the context information 12 are stored in a database 13 of patient data. Image analysis software executing on a data analysis server 14 then performs intelligent image processing and automated classification and quantification. The image analysis software is a computer program product tangibly embodied on a computer-readable storage medium in server 14 and comprises computer readable and executable program instructions that when executed by a processor on server 14 provide a visual display on a graphical user interface 15 of an interconnected display device 16, such as a personal computer. The image analysis software transforms weakly structured input data in the form of pixels into a hierarchical network of objects. This transformation occurs via a large number of intermediate steps, in which intermediate objects, which in the end are not relevant, are generated. These intermediate objects gradually develop into the ultimate relevant objects.

The image analysis program prepares links between some objects and thereby generates higher hierarchically ranked objects. The image analysis program provides the higher hierarchically ranked objects with properties, classifies them, and then links those objects again at a still higher level to other objects. The higher hierarchically ranked objects are used to find target objects in the images more rapidly. More easily detected starting objects are first found and then used to identify hard-to-find objects in the hierarchical data structure. Detecting hard-to-find target objects is faster using links in the hierarchical data network than using process-based procedures such as indexing.

Both general and subject-specific knowledge is used to classify and segment objects in the images. The knowledge and the program flow of the image analysis program are separated in the software structure. The parameters by which the image analysis is performed, for example thresholds of size or brightness, can be changed without having to revise the process hierarchy of software steps. The image analysis software displays both the original digital images 11 as well as the corresponding processed segmented images on the graphical user interface 15. Classified and segmented objects in the digital images are marked or highlighted to correspond to their classification. For example, objects that have a membership in the same class are depicted in the same color.

Figure 2:
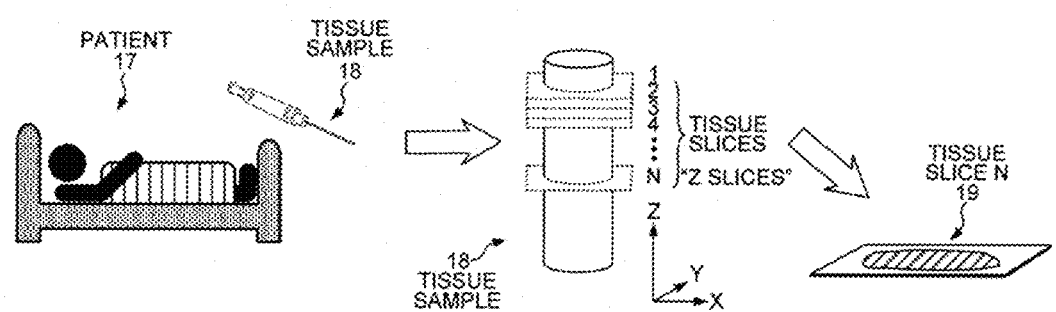
FIG. 2 illustrates the process for acquiring the digital images that are co-registered and displayed by the system of FIG. 1.

FIG. 2 illustrates the process for acquiring the digital images 11 that are co-registered and displayed by system 10. The tissue portions that are to be stained with various protein and receptor biomarkers are typically taken from a live patient 17 in the form of a biopsy. The tissue sample 18 is then sliced into many slices. The slices are called "z slices" because they depict the same position in the x and y dimensions of the tissue sample. FIG. 2 shows the nth slice 19 placed on a slide. Before being put on a slide, each of the multiple z slices is stained with a different biomarker. In fact, there are so many protein and receptor biomarkers that it is a challenge meaningfully to apply the information of how each different biomarker stain reacts with a tissue sample. In one embodiment, the process evaluates the results of a limited number of well known biomarkers, such as hematoxylin and eosin (HE), Human Epidermal growth factor Receptor 2 (Her2), Her2/neu cytoplasmic stain, estrogen receptor (ER) stain, progesterone receptor (PR) stain, tumor marker Ki67, Mib, SishChr17, SishHer2, cluster of differentiation 44 (CD44) antibody stain and CD23 antibody stain. A high resolution digital image 11 is then taken of each stained slice. A typical digital image of a tissue slice has a resolution of 100,000×200,000 pixels, or 20 billion pixels.

Because the z slices are very thin, each slice contains practically the same types of tissue. The same tissue reacts uniquely to each different biomarker. So the most meaningfully information can be obtained by comparing how the same particular tissue was stained by multiple different biomarkers. In order to determine which locations on different z slices corresponds to the same tissue, however, the digital images of the z slices must first be co-registered with one another.

Figure 4:
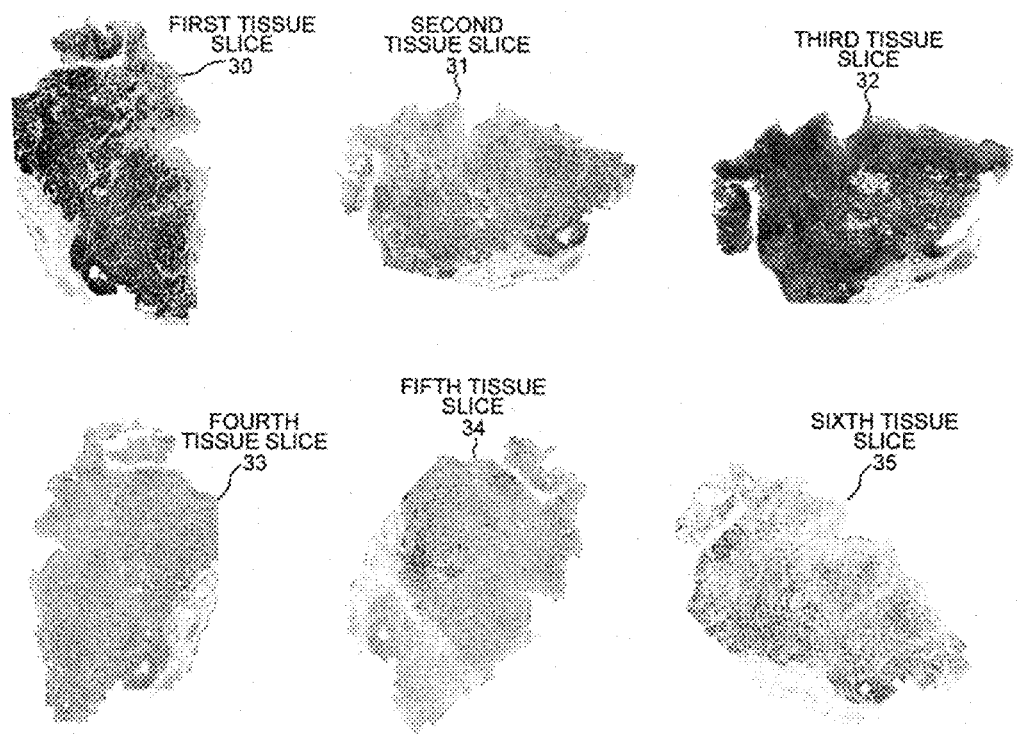
FIG. 4 shows high resolution images of six tissue slices that have been stained with different biomarkers.
Figure 3:
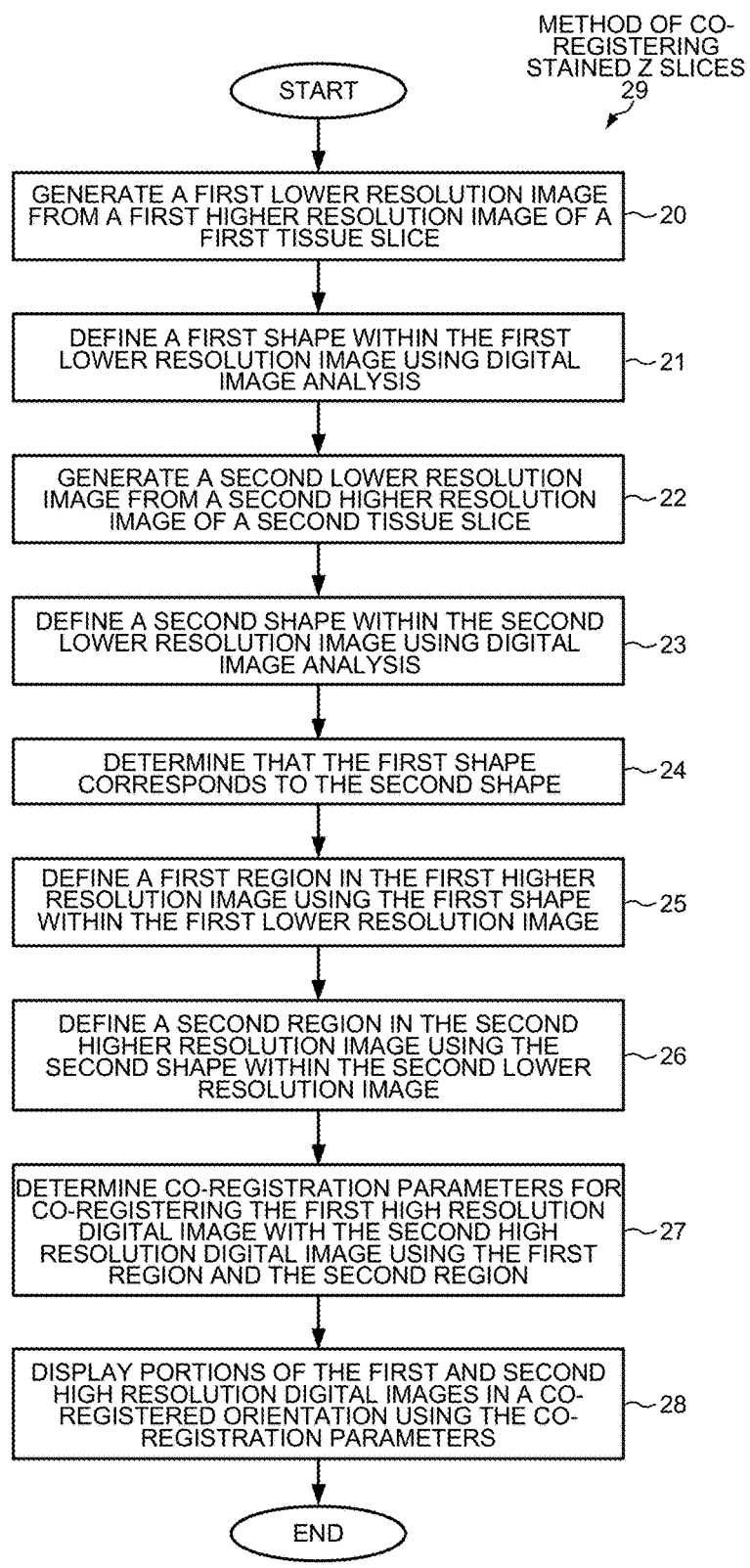
FIG. 3 is a flowchart of steps for co-registering digital images of differently stained z slices.

FIG. 3 is a flowchart of steps 20-27 of a method 29 of co-registering digital images of z slices stained by different biomarkers. In a first step 20, system 10 generates a low resolution image from the high resolution digital image 11 that was taken of each z slice. FIG. 4 shows the higher resolution digital images 30-35 of six tissue slices of the same tissue sample 18 that have been stained with different biomarkers. Note that when each z slice is removed from the staining solution, the slice may be in any orientation, for example, rotated about its center of gravity or flipped from its back side to front side. The higher resolution images 11 are acquired of the slices in whatever orientation those slices are placed on the slide after being pulled from the staining solution.

Figure 5:
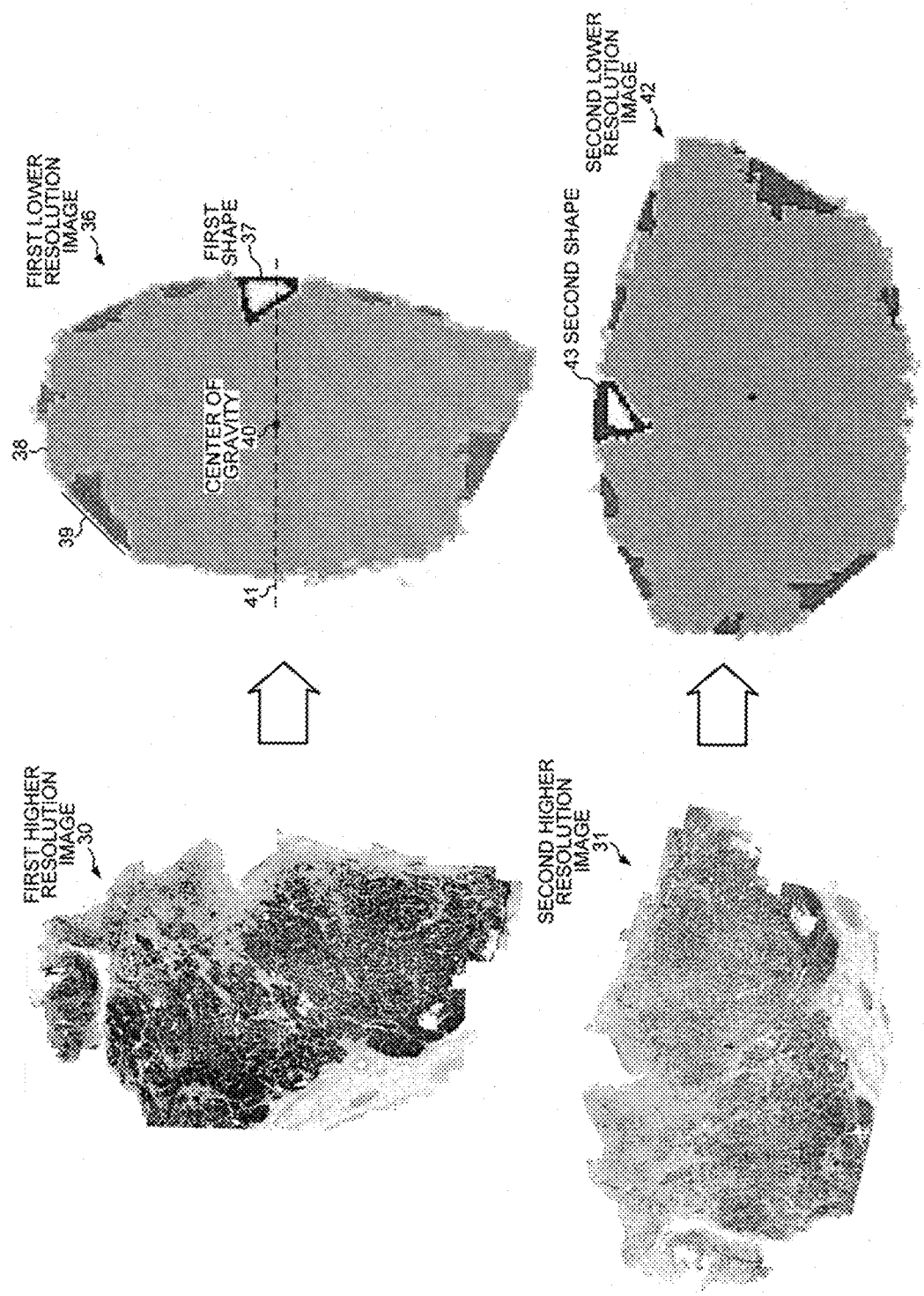
FIG. 5 illustrates how a lower resolution image is generated from a higher resolution image of a tissue slice.

FIG. 5 illustrates how, in step 20, a first lower resolution image 36 is generated from first higher resolution image 30 of the first tissue slice. Tissue structures are apparent in first higher resolution image 30, whereas only a rough outline of the z slice is depicted in first lower resolution image 36.

In step 21, a first shape 37 is defined within first lower resolution image 36 using digital image analysis. In one aspect, the image analysis program of system 10 uses object-oriented image analysis to generate an object 38 by linking all pixels of first lower resolution image 36 that belong to the z slice. Then first shape 37 is defined using the outline of the object by enclosing indentations in the outline. Each of these shapes around the outline includes a line 39 that connects an irregular-shaped indentation in the outline. FIG. 5 also shows the center of gravity 40 of the object 38 that depicts the z slice. Object-oriented image analysis is also used to find center of gravity 40. First shape 37 is defined in relation to center of gravity 40. Several shapes are generated around the perimeter of object 38. In one example, first shape 37 is identified as the largest shape nearest an axis 41 that passes through the center of gravity at the narrowest dimension of object 38. The largest shape can be defined as the shape that encloses the largest number of pixels.

Instead of using the outline of object 38 to form first shape 37, tissue objects may be used as first shape 37. For example, the image analysis program performs segmentation on first lower resolution image 36 to generate larger tissue objects such as blood vessels, glands or glomeruli. One of these tissue objects is then used a first shape 37.

In step 22, a second lower resolution image 42 is generated from second higher resolution image 31 of the second tissue slice. FIG. 5 also shows how second lower resolution image 42 is generated. Then in step 23, a second shape 43 is defined within the second lower resolution image 42 using digital image analysis. As with first shape 37, second shape 43 is also formed by enclosing an indentation in the outline of the object that depicts the z slice of second lower resolution image 42.

In step 24, the image analysis program of system 10 determines that first shape 37 corresponds to second shape 43. First shape 37 is determined to correspond to second shape 43 because the two shapes are similar and they are both located at similar positions relative to the axis that passes through the center of gravity at the narrowest dimension of each object.

In step 25, system 10 defines a first region 44 in first higher resolution image 30 using first shape 37 within first lower resolution image 36. The location of first region 44 in first higher resolution image 30 is defined based on the location of first shape 37 in first lower resolution image 36. In an alternative embodiment, by using two or three shapes in the lower resolution image, a region can be defined in the higher resolution image with greater accuracy.

Figure 6:
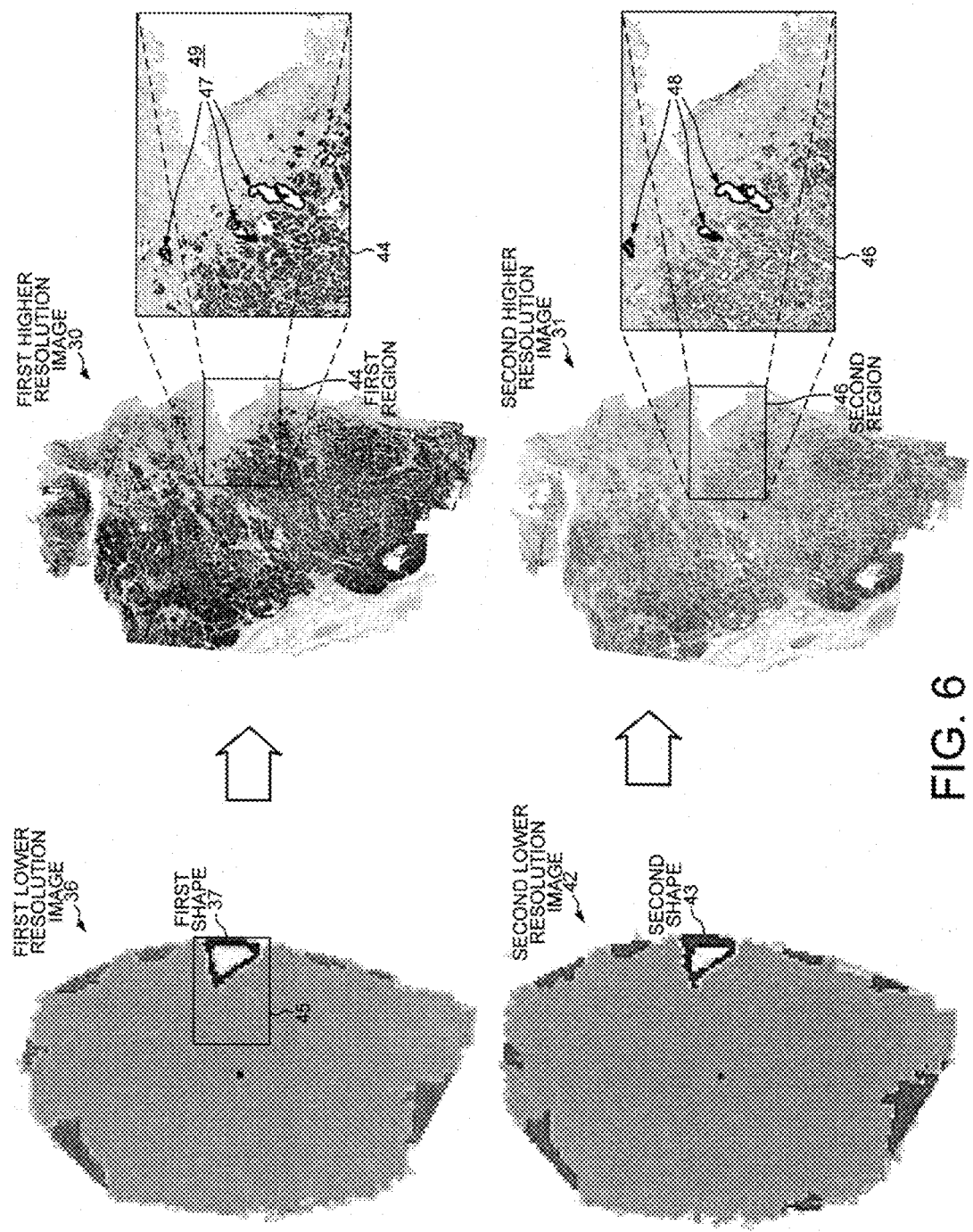
FIG. 6 illustrates how a region is defined in the higher resolution image of FIG. 5.

FIG. 6 illustrates how first region 44 is defined in first higher resolution image 30. In one embodiment, a low resolution region 45 is first defined in first lower resolution image 36 based on first shape 37. For example, a rectangular low resolution region is defined with one side that coincides with the line 39 that connects the irregular-shaped indentation of first shape 37. The location of low resolution region 45 first lower resolution image 36 is then mapped onto first higher resolution image 30 as first region 44. The correspondence between each pixel of first lower resolution image 36 and the pixels of first higher resolution image 30 that correspond to the lower resolution pixel is stored in data analysis server 14.

In step 26, system 10 defines a second region 46 in second higher resolution image 31 using second shape 43 within second lower resolution image 42.

In step 27, the image analysis program determines co-registration parameters for co-registering first high resolution digital image 30 with second higher resolution digital image 31 using first region 44 and second region 46. In one embodiment, at least three tissue structures 47 are identified in first region 44 that correspond to three tissue structures 48 in second region 46. The tissue structures 47-48 can be features in stroma tissue, blood vessels, glands or glomeruli. For example, a feature can be a cluster of epithelial cells within an environment of stroma cells. Alternatively, the contours of the edge of the tissue may also be used as the tissue structures, such as the 'bay" 49 in first region 44.

An affine transformation is then generated using the positions of the three tissue structures in both regions 44 and 46. By mapping each of the three structures in second region 46 to the corresponding structure in first region 44, all of the positions in second higher resolution digital image 31 can be interpolated linearly. In other embodiments, non-linear interpolation or piecewise interpolation is performed instead of the linear affine transformation. The co-registration of second higher resolution digital image 31 is performed by translating, rotating and scaling second higher resolution digital image 31 into a common coordinate system with first higher resolution image 30. Thus, the x-y coordinate systems of all higher resolution images of tissue slices 31-35 are calibrated so that the same physical structure that is present in the various digital images appears at the same x and y coordinates. The orientations of the first and second higher resolution images 30 and 31 in FIG. 6 have already been aligned for purposes of comparison. The image analysis program does not, however, align and co-register the images until after the tissue structures 47 and 48 are identified and the co-registration parameters are determined.

In another embodiment, two additional regions are defined in both first higher resolution image 30 and in second higher resolution digital image 31. Then only a single tissue structure is identified in each of the three regions of each higher resolution image. The tissue structure is located in each region of second higher resolution digital image 31 that corresponds to the tissue structure identified in each region of first higher resolution image 30. Thus, the image analysis program uses first shape 37 within first lower resolution image 36 to define three regions within first higher resolution image 30. The image analysis program also uses second shape 43 within second lower resolution image 42 to define three regions within second higher resolution image 31. Co-registration parameters for translating, rotating and scaling the x-y coordinate system of second higher resolution image 31 are then generated using the positions of the corresponding tissue structures in each of the three regions. The transformation parameters calculated using the location of the single tissue structure in each of the three regions are likely more accurate than the parameters calculated using the locations of three tissue structures in one region because the tissue structures in different regions will be spaced farther apart.

Figure 7:
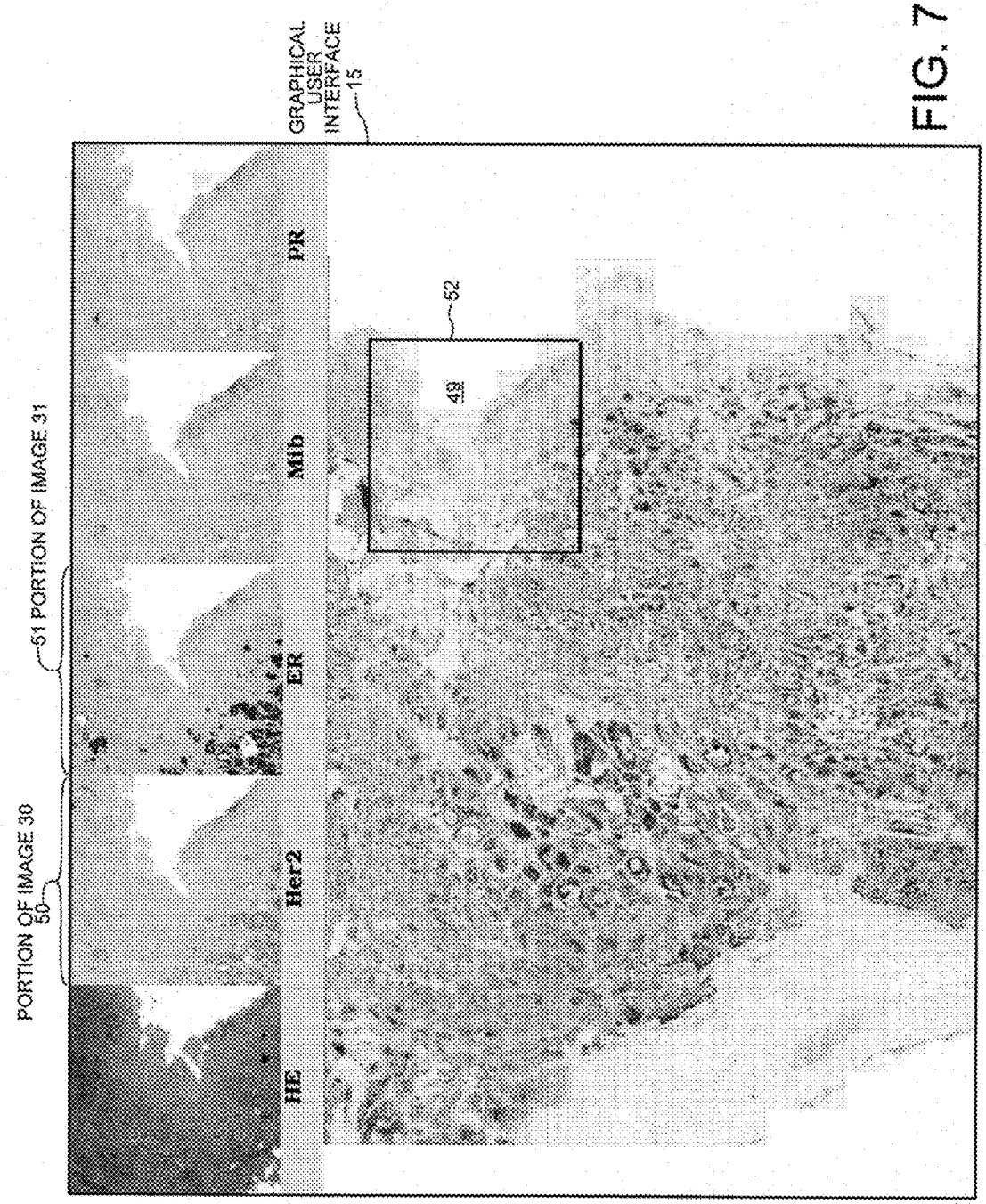
FIG. 7 is a screenshot of a graphical user interface on which co-registered image portions are displayed adjacent to one another.

In step 28, system 10 uses the co-registration parameters to display a portion 50 of first high resolution digital image 30 and a portion 51 of second high resolution digital image 31 in a co-registered orientation. FIG. 7 is a screenshot of graphical user interface 15 on which portions 50-51 are displayed adjacent to one another in a co-registered orientation.

In the example of FIG. 7, first higher resolution image 30 is an image of a tissue slice that has been stained with Human Epidermal growth factor Receptor 2 (Her2), whereas second higher resolution image 31 is an image of a tissue slice that has been stained with an estrogen receptor (ER) stain. Portions 50 and 51 of images 30 and 31 are displayed adjacent to one another in a co-registered orientation.

The combined view of stained slices can provide a more powerful diagnostic tool than the sum of individually displayed slices. For example, although a cancer region in one slice might be visible in a similar way in other stained slices, the heterogeneity of the tumor can be recognized with much higher precision by viewing adjacent co-registered images of stained slices. In one image, the cancerous regions might appear in a similar manner. In another image, the cancerous regions also might appear very similar. In a combined analysis of the two co-registered images, however, a heterogeneity might become apparent because the stained cancerous regions in one image appear in different x-y-locations than in the other image.

The image analysis program of system 10 is divided into modules. A computationally intensive co-registration module executes on the processor of data analysis server 14. Portions of co-registered high resolution images are then displayed by a display module on graphical user interface 15. The display module need not perform the calculations required to co-register the high-resolution images. The display module is a browser-based application that can be implemented as html code with embedded Java script. The display module executes on the processor of display device 16, which can be a personal computer, a laptop or a tablet such as an iPad®. In one aspect, the display module is a Java script viewer installed as an app on a tablet.

A user can inspect the tissue features in a high-resolution digital image of stained tissue in a manner similar to viewing the topography and landmarks of a map on the Google® Maps application. In addition to viewing the features of a first digital image of a z slice, however, the display module of system 10 permits the user simultaneously to view a portion of a second co-registered digital image of a differently stained z slice. The portion of the second image has the same shape as a frame that the user can move over the first image. The displayed portion of the co-registered second image coincides in the x and y dimensions with the area on the first image that is enclosed by the frame as the frame is shifted in the x and y dimensions over the first image. In one application, for example, the user is a physician running the display module as an app on a tablet. The physician can wirelessly download the co-registered images of stained biopsy z slices of his patients from database 13. As the physician examines his patients, the physician can locate a cancerous area in a larger first image of a tissue portion and compare how that cancerous area was stained by various biomarkers in other co-registered images. One of the co-registered images can be an unstained image of a z slice from the patient. Others of the images can be "object images" generated by the image analysis program from the co-registered images. The image analysis program segments and classifies objects in both stained or unstained images and then generates an object image with classified objects in the images highlighted. In FIG. 7, for example, the large lower image is an object image, and the square portions of other images that are displayed in a row on top are from tissue slices stained with the biomarkers HE, Her2, ER, Mib and PR. The portions of the images displayed in the top row coincide with the co-registered area enclosed by the frame 52 on the object image below. In other embodiments, the row of images of co-registered stained slices is displayed to the side of the large image or on the bottom of the large image. Frame 52 is displayed in FIG. 7 as a solid line in a square shape. In other embodiments, the line forming the frame can be dashed or dotted, and the shape can be any polygon or even circular. The frame can also be formed by crosses at the corners of the shape. Alternatively, the frame is not displayed, but the area within the frame is indicated by a cross-hair at the center of the area of the transparent frame.

Figure 8:
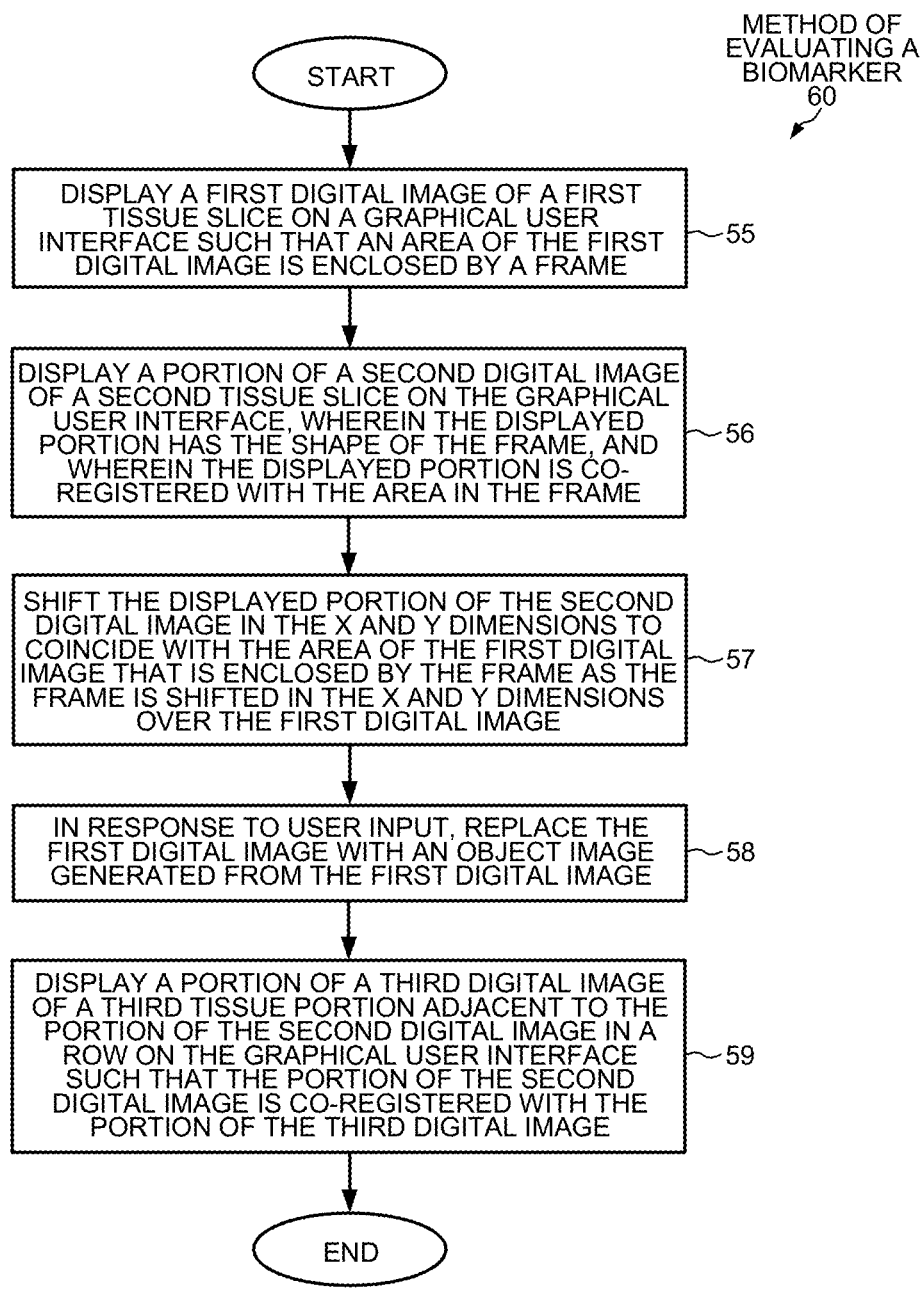
FIG. 8 is a flowchart of steps for simultaneously displaying co-registered digital images of tissue slices that have been stained by different biomarkers.

FIG. 8 is a flowchart of steps 55-59 of a method 60 for simultaneously displaying co-registered digital images of tissue slices that have been stained by different biomarkers. The steps of method 60 are described in relation to the graphical user interface 61 shown in FIG. 9.

Figure 9:
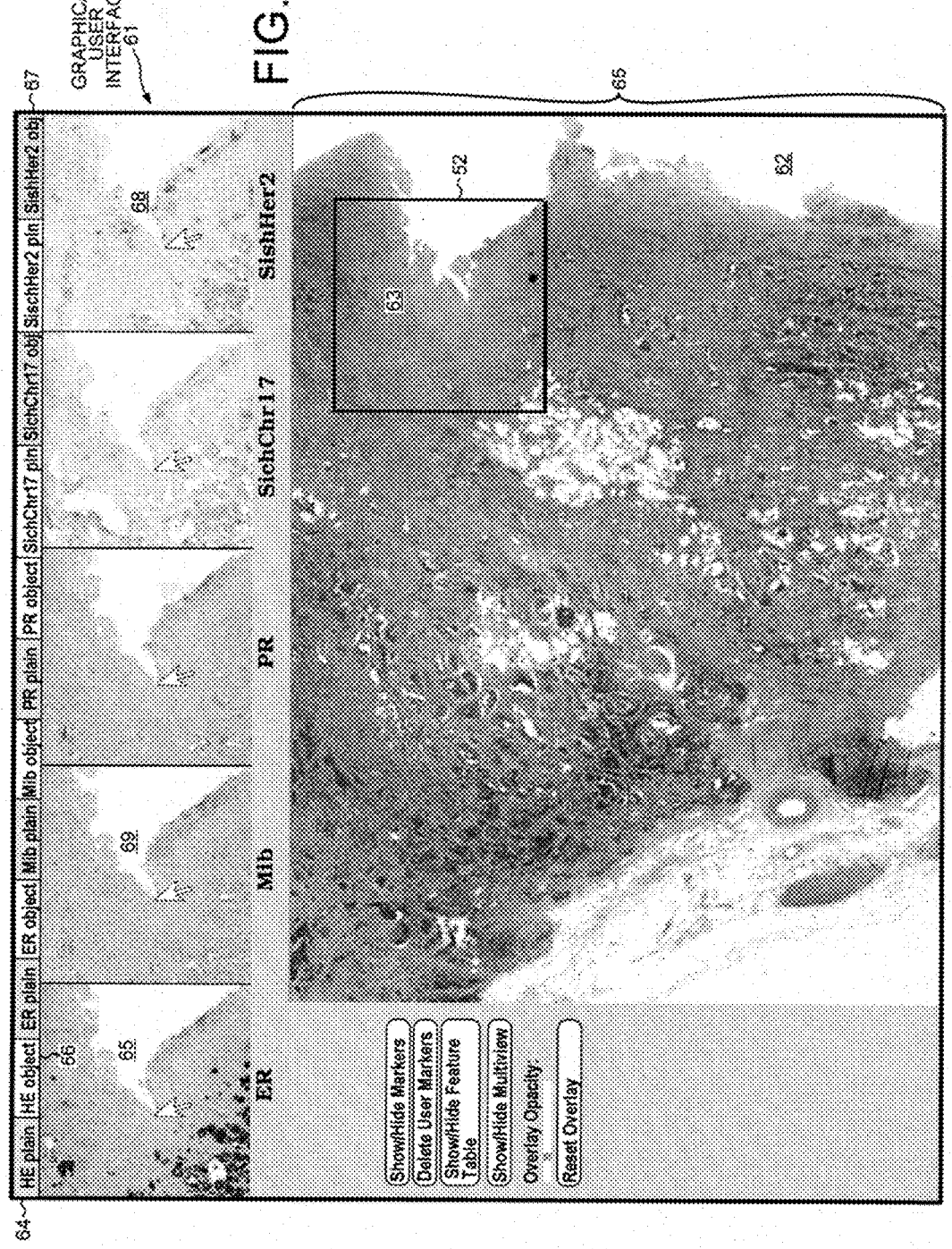
FIG. 9 is a screenshot of a graphical user interface with a moveable frame over a larger image below a row of five differently stained, co-registered image portions.

In a first step 55, the display module of the image analysis program displays a first digital image 62 of a first tissue slice on graphical user interface 61 such that an area 63 of first digital image 62 is enclosed by frame 52. First digital image 62 is the large image towards the bottom of graphical user interface 61. In the example of FIG. 9, first digital image 62 is a high resolution image of tissue that has been stained by the hematoxylin and eosin (HE) stain. Image 62 has about 20 billion pixels. Graphical user interface 61 includes an indicator tab 64 indicating that the large first digital image 62 is a plain image as opposed to an object image.

In step 56, a portion 65 of a second digital image of a second tissue slice is displayed on graphical user interface 61. The displayed portion 65 of the second digital image has the shape of frame 52. Although in the example of FIG. 9 both frame 52 and the displayed portion 65 are square, both frame 52 and portion 65 could have another rectangular shape. Both the first and second tissue slices that are depicted in the first and second digital images are z slices taken from a tissue sample at corresponding positions in the x and y dimensions, such as those shown in FIG. 2. The area 63 of the first digital image that is enclosed by frame 52 corresponds to the displayed portion 65 of the second digital image. As displayed on graphical user interface 61, the area 63 of the first digital image that is enclosed by frame 52 is co-registered with the displayed portion 65 of the second digital image. Thus, corresponding tissue structures appear at the same x and y coordinates in both frame 53 and portion 65. In the example of FIG. 9, the second digital image that includes portion 65 is a high resolution image of tissue that has been stained by the estrogen receptor (ER) stain. In one aspect, the user of system 10 can improve upon the co-registration between area 63 and portion 65 by clicking and holding the cursor on portion 65 and then shifting portion 65 in the x and y dimensions for a better correspondence with the image features in area 63.

In step 57, the display module shifts the displayed portion 65 of the second digital image in the x and y dimensions to coincide with the area 63 of the first digital image that is enclosed by frame 52 as the user shifts frame 52 in the x and y dimensions over the first digital image 62. In a first embodiment, the user selects frame 52 with the cursor and holds the cursor clicked while shifting frame 52 over first digital image 62. The display module then shifts the displayed portion 65 to correspond to the area 63 enclosed by frame 52 as the user shifts frame 52 over the first digital image 62. Clicking on large first digital image 62 toggles the image between the plain version and the object image.

In a second embodiment, the user selects any location on large first digital image 62 and holds the cursor clicked in order to drag image 62 and thereby shift image 62 in the x and y dimensions under a stationary frame 52. The display module then shifts the displayed portion 65 of the second digital image to correspond to the area 63 of the first digital image that is enclosed by frame 52 as the user shifts the first digital image 62 under frame 52. In the second embodiment, frame 52 is located towards the center of the pane 65 in which large first digital image 62 is displayed. Then the user shifts various regions of first digital image 62 into the view of pane 65. In the first embodiment, the portion of large first digital image 62 that is visible in pane 65 is fixed, and the user can shift frame 52 throughout pane 65. The entire image 62 of the first tissue slice can be inspected in the second embodiment at a higher magnification than in the first embodiment because frame 52 can pass over only that portion of fixed image 62 in the first embodiment that can be displayed in pane 65. At a very high magnification, the image of the entire first tissue slice will not fit in pane 65.

In step 58, the first digital image 62 is replaced with an object image generated from the first digital image 62. In response to the user of system 10 clicking on any location in large first digital image 62 in the first embodiment, the display module toggles the image displayed in pane 65 between the plain version and the object image. The object image depicts objects that are generated by segmenting the first digital image 62 into classified objects. Just as for the plain image, the area 63 of the object image that is enclosed by frame 52 is co-registered with the displayed portion 65 of the second digital image.

In the second embodiment, the first digital image 62 is replaced with an object image in response to the user of system 10 clicking on an indicator tab 66 that when highlighted indicates that the image displayed in pane 65 is an object image. In FIG. 9, a highlighted indicator tab 67 indicates that the portion 68 of a digital image that is displayed at the far-right of the row of square image portions is an object image generated from an image of a tissue slice that has been stained with Silver In Situ Hybridization Her2 (SishHer2) stain.

In step 59, a portion 69 of a third digital image of a third tissue slice is displayed on graphical user interface 61 next to portion 65. In the example of FIG. 9, the third digital image is a high resolution image of tissue that has been stained by the monoclonal antibody Mib-1 stain. The display module displays the third digital image adjacent to the second digital image in the row of square image portions above pane 65. The first, second and third tissue portions are all z slices taken from the same tissue sample at corresponding positions in the x and y dimensions. Each of portions 65 and 69 of the second and third digital images has the shape of frame 52, and the area 63 of first digital image 62 that is enclosed by frame 52 is co-registered with both portion 65 and portion 69. Although the row of images of co-registered stained slices is displayed in FIG. 9 on top of large digital image 62, in other embodiments the row of co-registered images is displayed to the side of the large image or on the bottom of the large image.

The third digital image also shifts in the x and y dimensions to coincide with the area 63 of first digital image 62 that is enclosed by frame 52 as first digital image 62 is shifted in the x and y dimensions under frame 52. Thus, system 10 allows the user simultaneously to view multiple adjacent co-registered images in order to compare how a tissue feature has been stained by different biomarkers in each image. FIG. 9 shows five adjacent co-registered image portions that are stained with different biomarkers and that all shift in the x and y dimensions to coincide with the area 63 within frame 52 as first digital image 62 is shifted in the x and y dimensions under frame 52. For example, a physician diagnosing the malignancy of breast cancer in a tissue sample can easily and intuitively inspect how tumor cells that the physician has located in large first digital image 62 using a first biomarker stain are stained by five other biomarkers.

In a co-registration mode, the user of system 10 can improve upon the co-registration between the image portions in the row above pane 65 by marking corresponding tissue structures in different image portions with the cursor. For example, the dashed cursors in FIG. 9 illustrate how the user marks the tip of the "bay" in each tissue portion. The image analysis program then adds those points to the features used to calculate the co-registration parameters between the various image portions.

Figure 10:
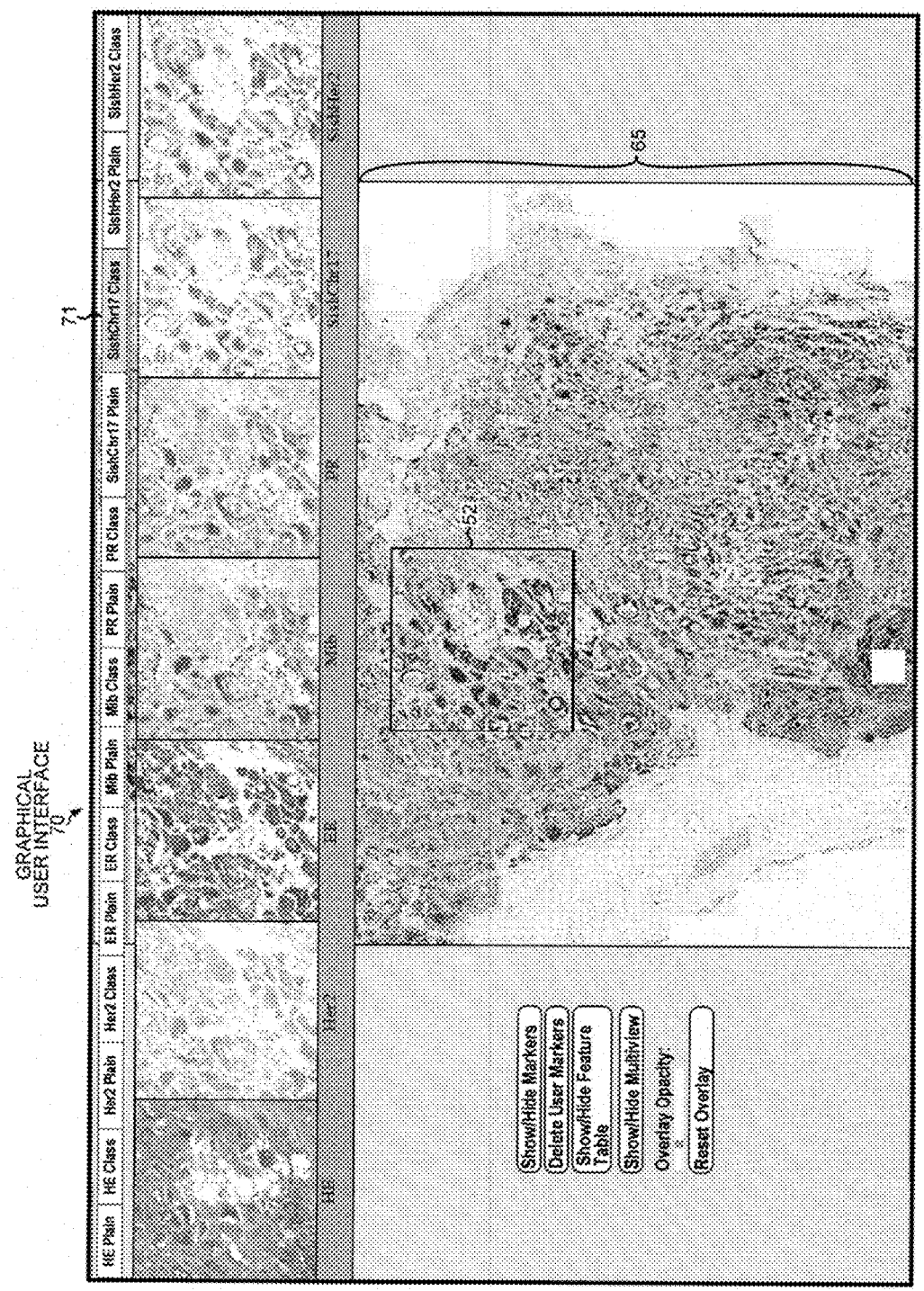
FIG. 10 is a screenshot of a graphical user interface with a fixed frame towards the middle of a larger image below a row of seven co-registered image portions.

FIG. 10 is a screenshot of a graphical user interface 70 of system 10 with a row of seven adjacent co-registered image portions that are stained with different biomarkers. FIG. 10 illustrates the second embodiment in which frame 52 is located towards the center of pane 65 in which a large digital image is displayed. As the user shifts the large digital image under frame 52, the display module shifts the portions of the images displayed in the row above such that those portions remain co-registered with the area of the large digital image that is enclosed by frame 52. The highlighted indictor tab 71 in FIG. 10 indicates that the large digital image displayed in pane 65 is an object image in which objects stained by Silver In Situ Hybridization chromosome 17 (SishChr17) stain have been segmented, classified and highlighted.

Figure 11:
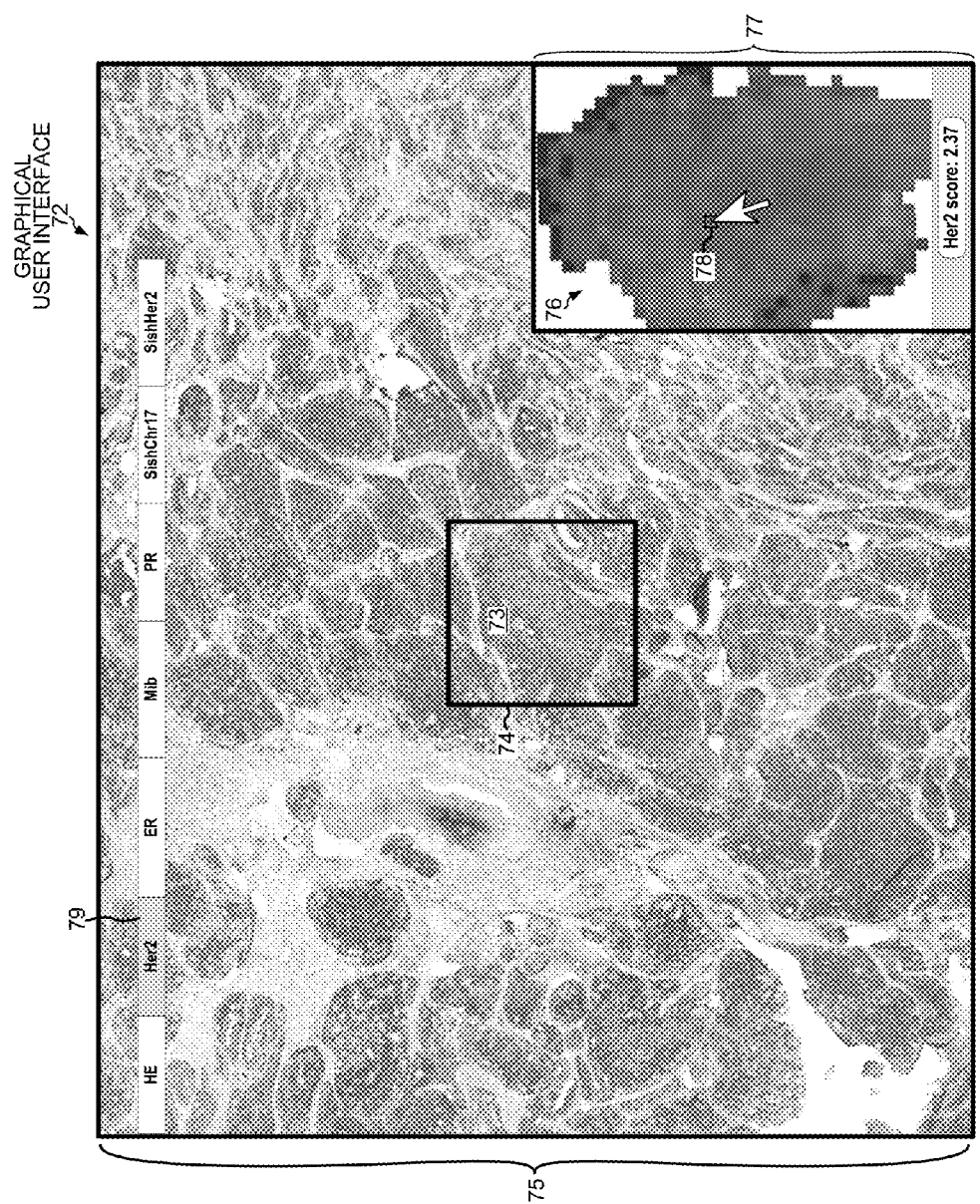
FIG. 11 is a screenshot of a graphical user interface on which score-driven navigation is performed using a smaller tiled representation of a larger, higher-resolution image on which a frame is centered.

System 10 can also perform score-driven navigation within stained digital images. FIG. 11 shows a screenshot of a graphical user interface 72 generated by system 10 as the display module performs score-driven navigation. The image analysis program performs a local statistical evaluation on individual regions within a high resolution digital image of a stained tissue slice. The image of the stained tissue slice is divided into a matrix of tile regions. FIG. 11 shows a tile region 73 of a high resolution image enclosed by a frame 74 in the main pane 75 of graphical user interface 72. The image analysis program statistically evaluates the degree and character of the staining in each tile region and assigns a staining score to each tile region. The display module displays a small tiled representation 76 of the high resolution image in an inset pane 77 on graphical user interface 72 of system 10. The shade or color of each tile of tiled representation 76 represents the staining score assigned to the corresponding tile region of the high resolution image. When the user of system 10 clicks on a tile of tiled representation 76, the display module indicates the staining score for the associated tile region in a field below tiled representation 76.

In addition, system 10 navigates to the associated tile region in the high resolution image when the user clicks on a tile of tiled representation 76. When a tile is clicked, the display module shifts the high resolution image such that the associated tile region is enclosed by frame 74. FIG. 11 illustrates that in response to a user clicking on tile 78 of tiled representation 76, display module has shifted the high resolution image under frame 74 such that tile region 73 is within frame 74. In this manner, the user of system 10 can visually locate high or low scoring tiles in tiled representation 76 and then conveniently inspect the stained tissue that produced the high or low score. In a situation in which tile region 73 was initially outside the field of view of graphical user interface 72 when the user selected tile 78, system 10 shifts tile region 73 into the field of view and tile region 73 becomes visible on graphical user interface 72 when the user clicks on tile 78.

In another embodiment, system 10 performs the score-driven navigation without using frame 74 or the tiles of the representation 76. System 10 navigates to an unmarked region in a higher resolution image that corresponds to a location on a corresponding lower resolution image that the user has selected. The image in main pane 75 is the higher resolution image, and the representation in inset pane 77 is the lower resolution image. System 10 displays a portion of the higher resolution image on graphical user interface 72; the remainder of the higher resolution image is outside the field of view of graphical user interface 72 and is not visible to the user. The image analysis program divides the higher resolution image into regions whose boundaries are not marked on graphical user interface 72.

For example, the location of the lower resolution image is defined as a pixel of the lower resolution image. Each pixel of the lower resolution image corresponds to multiple pixels of the higher resolution image. Thus, regions of the higher resolution image can be overlapping in the x and y dimensions. A first region of the higher resolution image that corresponds to a first location of the lower resolution image overlaps a second region of the higher resolution image that corresponds to an adjacent second location of the lower resolution image. Each region of the higher resolution image whose boundary is unmarked can be defined by the pixels within a predetermined shape. For example, the pixels in a circle or a rectangle centered around a particular pixel of the higher resolution make up the predetermined shape of the region of the higher resolution image.

The image analysis program then generates a statistical value associated with each of the regions, such as a staining score. The display module generates a lower resolution image from the higher resolution image such that each location on the lower resolution image corresponds to a region of the higher resolution image. Each location on the lower resolution image has an appearance indicative of the statistical value associated with the corresponding region on the higher resolution image. The indicative appearance can be a color, a shade of gray or a texture. In one situation, a selected location on the lower resolution image corresponds to a first region on the higher resolution image that is not visible because the first region is outside the field of view of graphical user interface 72. In response to a user selecting the selected location on the lower resolution image, display module shifts the higher resolution image on graphical user interface 72 such that the first region moves into the field of view and becomes visible on graphical user interface 72.

When the user clicks on an indicator tab associated with a different biomarker, the display module displays a tiled representation of the scores for the selected biomarker stain. When the user clicks on the selected indicator tab, the display module also displays in main pane 75 the high resolution image of the tissue slice stained by the selected biomarker stain. Multiple scoring methods are possible to interpret the same stained tissue slice. System 10 can also generate user-defined, object-based scores from objects stained by a particular biomarker. For example, an object-based score could be the quotient of the number of darkly stained nuclei in a tile region divided by the total number of nuclei in the tile region.

In the example of FIG. 11, an indicator tab 79 indicates that tiled representation 76 represents the Her2 scores for the tile regions of the high resolution image. The Her2 score ranges from 0 through 3+ and indicates the severity of breast cancer. The score represents the level of Her2 protein overexpression based on the degree of membrane staining. Complete membrane staining of some tumor cells results in a score of 3+ irrespective of the percentage of tumor cells that are stained. The image analysis program is able to determine whether each membrane object has the stain color around the entire membrane. Thus, the image analysis program searches for "0" shaped Her2 staining as opposed to "U" shaped or "||" shaped staining.

Tiled representation 76 can represent other staining scores as well, such as the Allred score, the Gleason score, or the Elston-Ellis score. In each case, the image analysis program calculates the score separately for each tile region of each high resolution image. The Allred score ranges from 0-8 and indicates the percentage of cells in a region that have been stained to a certain intensity by the estrogen receptor (ER) antibody. Thus, the Allred score is the composite of a proportion score and an intensity score. The Allred score is indicative of breast cancer. An Allred score of three or more indicates ER positivity and can correspond to as few as 1% of the cells in the region showing a weak immunostaining signal. The image analysis program calculates the Allred score by segmenting cell objects and then determining the average intensity of the staining color in the pixels within the cell objects.

The Gleason score ranges from 1-5 and is indicative of prostate cancer. The Gleason score is based on the architectural pattern of the glands of the prostate tumor. Cancer cells that are not able to structure themselves into glands resembling those of the normal prostate are assigned a score of five signifying aggressively malignant, whereas cancer cells that have a normal gland architecture are assigned a score of one signifying not very malignant. By generating hierarchically ranked objects in a hierarchical data network, the image analysis program is able to classify gland objects made up of cancer cells as having a normal gland architecture or various degrees of undifferentiated architectures. A Gleason score is calculated for each tile region of each high resolution image.

The Elston-Ellis score is a grade ranging from I-III indicative of the severity of breast cancer. A grade of III indicates the most aggressive cancer, whereas the tumor cells of grade I breast cancer are not dividing rapidly. The grade is determined by summing the points assigned to three parameters: tubule formation, nuclear pleomorphism and mitosis per region. A region of ten high-power fields (HPF) of 400× is often used in the Elston-Ellis test. Thus, in determining the Elston-Ellis score, the image analysis program divides the high resolution image into tile regions of ten HPF. Each of the parameters can have a point score ranging from 1-3 (1 being the best, and 3 being the worst). Thus, a sum of three results in a grade of I, whereas a sum of nine results in a grade of III. The image analysis program is able to determine the proportion of tubules, the similarity of nucleus sizes and the number of dividing cells per region.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method comprising:
   displaying a first digital image of a first tissue slice on a graphical user interface such that an area of the first digital image is enclosed by a frame, wherein the displayed portion of the first digital image is larger than the frame;
   displaying a portion of a second digital image of a second tissue slice on the graphical user interface, wherein the first tissue slice and the second tissue slice are both z slices taken from a tissue sample at corresponding positions in the x and y dimensions, wherein the displayed portion of the second digital image has a shape of the frame, wherein the area of the first digital image that is enclosed by the frame corresponds to the displayed portion of the second digital image, wherein the area of the first digital image that is enclosed by the frame is co-registered with the displayed portion of the second digital image; and
   shifting the displayed portion of the second digital image in the x and y dimensions to coincide with the area of the first digital image that is enclosed by the frame as the frame is shifted in the x and y dimensions over the stationary first digital image.

2. The method of claim 1, wherein the first tissue slice is stained with a first biomarker, and wherein the second tissue slice is stained with a second biomarker.

3. The method of claim 2, wherein the first biomarker is taken from the group consisting of: hematoxylin and eosin (HE), Human Epidermal growth factor Receptor 2 (Her2), estrogen receptor (ER) stain, progesterone receptor (PR) stain, Silver In Situ Hybridization chromosome 17 (Sish-Chr17) stain, Silver In Situ Hybridization Her2 (SishHer2) stain, and monoclonal antibody Mib-1 stain.

4. The method of claim 1, further comprising:
   replacing the first digital image with an object image generated from the first digital image, wherein the object image depicts objects that are generated by segmenting the first digital image, and wherein an area of the object image that is enclosed by the frame is co-registered with the displayed portion of the second digital image.

5. The method of claim 4, wherein the first digital image is replaced with the object image in response to clicking on the first digital image.

6. A method comprising:
   displaying a first digital image of a first tissue portion on a graphical user interface such that an area of the first digital image is enclosed by a frame, wherein the displayed portion of the first digital image is larger than the frame;
   displaying a second digital image of a second tissue portion on the graphical user interface; and
   displaying a third digital image of a third tissue portion on the graphical user interface adjacent to the second digital image, wherein the first, second and third tissue portions are z slices taken from a tissue sample at corresponding positions in the x and y dimensions, wherein each of the second digital image and the third digital image has a shape of the frame, wherein the area of the first digital image that is enclosed by the frame is co-registered with both the second digital image and the third digital image, and wherein the second digital image shifts in the x and y dimensions to coincide with the area of the first digital image that is enclosed by the frame as the first digital image is shifted in the x and y dimensions under the stationary frame.

7. The method of claim 6, wherein the second digital image and the third digital image are displayed in a row above the first digital image.

8. The method of claim 6, wherein the first tissue portion is stained with a first biomarker, and wherein the second tissue portion is stained with a second biomarker.

9. The method of claim 6, wherein the second digital image borders the third digital image.

10. The method of claim 6, further comprising:
replacing the second digital image with an object image generated from the second digital image, wherein the object image depicts objects that are generated by segmenting the second digital image, and wherein the object image is co-registered with the area of the first digital image that is enclosed by the frame.

11. A method comprising:
displaying a first digital image of a first tissue slice on a graphical user interface such that an area of the first digital image is enclosed by a frame, wherein the displayed portion of the first digital image is larger than the frame;
displaying a portion of a second digital image of a second tissue slice on the graphical user interface, wherein the displayed portion of the second digital image has a size of the frame, wherein the area of the first digital image that is enclosed by the frame corresponds to the displayed portion of the second digital image, wherein the area of the first digital image that is enclosed by the frame is co-registered with the displayed portion of the second digital image; and
shifting the displayed portion of the second digital image to coincide with the area of the first digital image that is enclosed by the frame in response to a user shifting the frame relative to the first digital image, wherein the frame is shifted relative to the first digital image by shifting the frame over the stationary first digital image or by shifting the first digital image under the stationary frame.

12. The method of claim 11, wherein the user shifts the first digital image under the frame by clicking on the first digital image and then moving a mouse.

13. The method of claim 11, wherein the first tissue slice is stained with a first biomarker, and wherein the second tissue slice is stained with a second biomarker.

14. The method of claim 13, wherein the first biomarker is taken from the group consisting of: hematoxylin and eosin (HE), Human Epidermal growth factor Receptor 2 (Her2), estrogen receptor (ER) stain, progesterone receptor (PR) stain, Silver In Situ Hybridization chromosome 17 (Sish-Chr17) stain, Silver In Situ Hybridization Her2 (SishHer2) stain, and monoclonal antibody Mib-1 stain.

15. The method of claim 11, further comprising:
replacing the first digital image with an object image generated from the first digital image, wherein the object image depicts objects that are generated by segmenting the first digital image, and wherein an area of the object image that is enclosed by the frame is co-registered with the displayed portion of the second digital image.

16. The method of claim 15, wherein the first digital image is replaced with the object image in response to clicking on the first digital image.

17. The method of claim 11, wherein the frame is shifted relative to the first digital image by shifting the first digital image under the frame, and wherein the frame is present at a fixed location on the graphical user interface over the first digital image.

* * * * *